(12) United States Patent
Patterson

(10) Patent No.: US 6,675,103 B1
(45) Date of Patent: Jan. 6, 2004

(54) VISUALIZING HIGH DIMENSIONAL DESCRIPTORS OF MOLECULAR STRUCTURES

(75) Inventor: David E. Patterson, St. Louis, MO (US)

(73) Assignee: Tripos, Inc., St. Louis, MO (US)

( * ) Notice: Subject to any disclaimer, the term of this patent is extended or adjusted under 35 U.S.C. 154(b) by 0 days.

(21) Appl. No.: 09/533,035

(22) Filed: Mar. 22, 2000

(51) Int. Cl.[7] .................... C12Q 1/00; G01N 33/566; G01N 33/48; G01N 31/00
(52) U.S. Cl. .................. 702/19; 435/4; 702/22; 702/27; 702/30; 436/501
(58) Field of Search ............... 702/19, 22, 30, 702/27; 435/DIG. 1, DIG. 51; 436/501

(56) References Cited

PUBLICATIONS

Domine et al., J. Chemometrics, 1993, vol. 7, pp. 227–242.*
Agrafiotis D. K., J. Chem. Inf. Comput. Sci. 1997, vol. 37, pp. 841–851.*

* cited by examiner

Primary Examiner—John S. Brusca
Assistant Examiner—Shubo "Joe" Zhou
(74) Attorney, Agent, or Firm—Laurence A. Weinberger

(57) ABSTRACT

The distribution of chemical compounds in high-dimensional molecular descriptor space can be viewed in two dimensions by applying the projection method of this invention. This method has particular usefulness for viewing the relationships of a large number of compounds such as found in a large scale HTS or virtual combinatorial library. After selecting a representative subset of the larger data set of comounds, initially components from the high-dimensional descriptor space are determined by PCA. In order to relax an NLM projection using the PCA components as a start, the stress function is modified to reflect a local horizon beyound which the separation of the compounds is not meaningfully measureable. The resulting two dimensional projections provide a clear insight into the distribution of the chemical compounds in the higher dimensional space.

1 Claim, 13 Drawing Sheets

VISUALIZING HIGH DIMENSIONAL DESCRIPTORS OF MOLECULAR STRUCTURES

A computer program listing appendix is part of the disclosure and is incorporated herein by reference. The computer program listing appendix contained on compact disks contains the following files: Identification Information (1KB) and NLMJER.C (20KB). The disks were created on Sep. 15, 2003.

BACKGROUND OF THE INVENTION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

1. Field Of The Invention

This invention relates to the field of computational molecular structural analysis of large data sets of molecular structures and more specifically to graphical displays that present an accurate qualitative representation of the distribution of molecular structures in the high dimensional space of molecular descriptors.

2. Background Of The Art

With the advent of high throughput screening (HTS), combinatorial synthesis, and analysis and selection of compounds from computer generated virtual libraries, research scientists, and pharmaceutical scientists in particular, are faced with an expanding problem of separating compounds of most significance to their work from a clutter of possibilities. In recent years an appreciation has developed that: 1) it is useful to think about how molecular structures populate a "diversity space" of all possible structures; 2) that structures generated from different synthetic routes may populate the same or different volumes of diversity space; and 3) that broad based screening programs should utilize compounds from across diversity space and avoid over-screening with compounds that densely occupy the same volume of diversity space.

Scientists in drug discovery research make decisions each day that affect the course of their projects. A decade ago, decisions were based on infrequent new biological data, and resulted in making small numbers of compounds per year. Today, high throughput screening laboratories generate a constant stream of new biological data and call for larger numbers of new compounds to be made ever faster by combinatorial chemistry laboratories.

Decisions about which compounds to acquire or synthesize to test next are based in part on the output of computations utilizing advanced molecular structural descriptors. The simplest drug discovery principle is that compounds similar in enough properties are usually similar in biological activity. Similarity often involves measures in high-dimensional spaces, such as molecular fingerprints or shape descriptors which typically utilize around one-thousand dimensions. Uses of similarity in drug discovery research may apply these high-dimensional descriptors to millions of compounds from virtual libraries of potentially synthesizable compounds or to libraries of synthesized compounds which have been generated.

SUMMARY OF THE INVENTION

The method of this invention enables scientists to examine relationships among the vast numbers of compounds in high-dimensional diversity space in a familiar two-dimensional visual map context. The method for visualization of high-dimensional diversity spaces relies on the implementation of horizons, which are distances beyond which the distance matrix between compounds need not be resolved, and on efficient subsampling methods. The method also enables the selection of optimal descriptors to cluster compounds for predictive use when combined in genetic algorithms. Optimal descriptors help not only in visualizing important features of diversity space, but in deciding which compounds to make and test next during early analoging of active substances.

DESCRIPTION OF THE INVENTION

Computational Chemistry Environment

Figure 1:
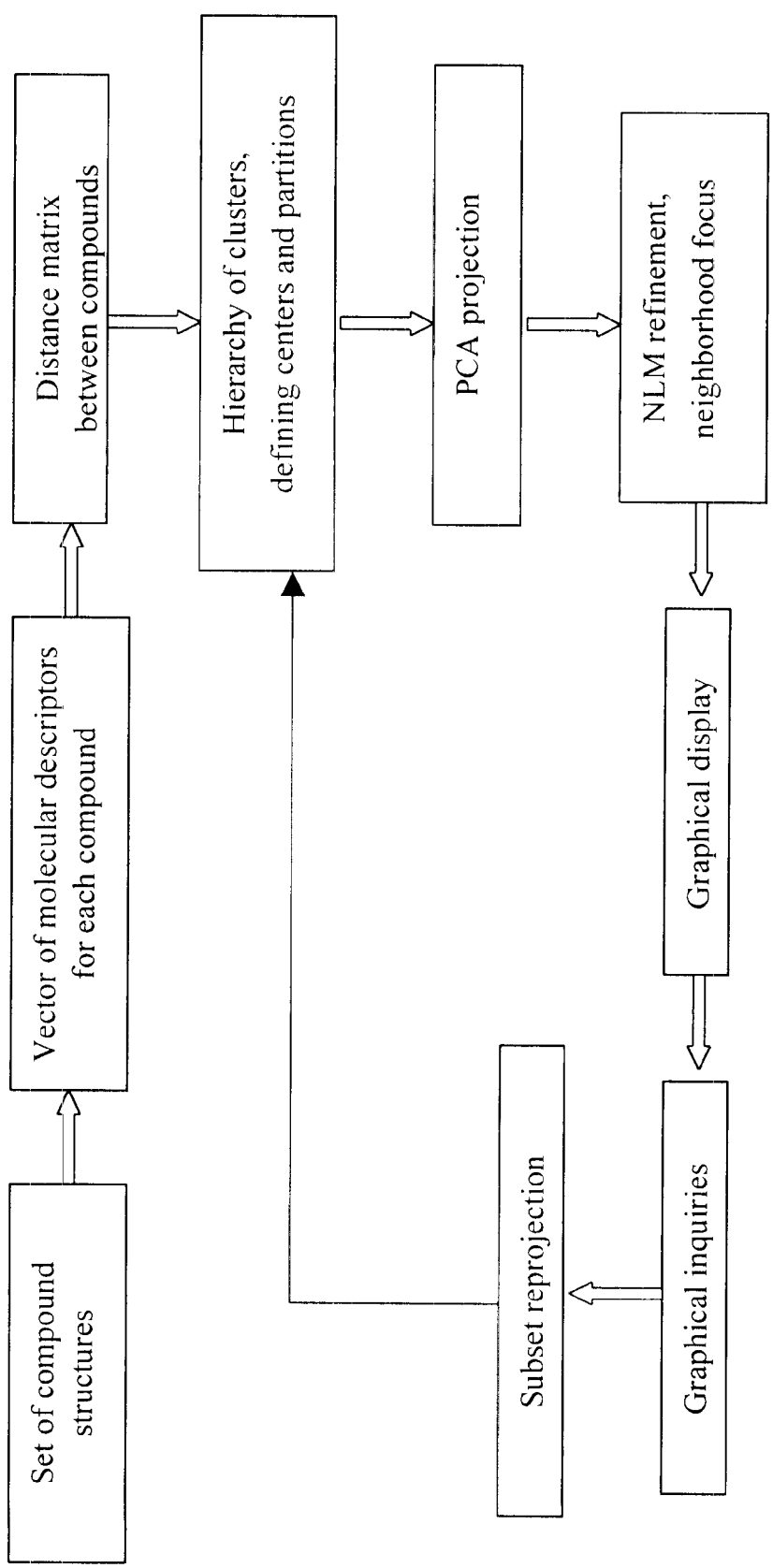
FIG. 1 shows a schematic outline of the process of the invention.

Generally, all calculations and analyses to generate the visualizations of this invention are implemented in a modern computational chemistry environment using software designed to handle molecular structures and associated properties and operations. For purposes of this patent document, such an environment is specifically referenced. In particular, the computational environment and capabilities of the SYBYL and UNITY software programs developed and marketed by Tripos, Inc. (St. Louis, Mo.) are specifically utilized. Unless otherwise noted, all software references and commands in the following text are references to functionalities contained in the SYBYL and UNITY software programs. Where a required functionality is not available in SYBYL or UNITY, the software code to implement that functionality is provided in an Appendix to this Application. Software with similar functionalities to SYBYL and UNITY are available from other sources, both commercial and non-commercial, well known to those in the art. A Java enabled computing environment for graphical interface is also referenced. A general purpose programmable digital computer with ample amounts of memory and hard disk storage is required for the implementation of this invention. In performing the methods of this invention, representations of thousands of molecules and molecular structures as well as other data may need to be stored simultaneously in the random access memory of the computer or in rapidly available permanent storage. The inventors use a 150 Mhz R4400 SGI computer with an R4010 floating point processor, 128 Mbytes of memory, disk space locally and on a network with no specific quota, access to graphics from other SGI consoles as well as via X windows on PCs and X terminals.

Definitions

Explicit library: a collection of compounds in which each compound has an explicit structure. Corporate compound library databases at pharmaceutical companies fall in this category.

Fingerprints: a vector of binary variables that represents the presence or absence of 2D molecular fragments in a molecule. In this patent document fingerprints refer specifically to the 988 binary variables used for the past several years in the Unity structural database definition, in which all possible fragments of length 2 to 6 are hashed together and key heteroatoms (O,N,S,P, Si, halogens) and rings are counted.

Horizon: a distance beyond which all points are indistinguishable.

NLM: non-linear mapping. This algorithm attempts to minimize the overall fractional error in preserving the actual distances in many dimensions when going to fewer dimensions. Modifying this algorithm is a key part of the present invention.

PCA: principal component analysis. This mathematical method is used to select an initial guess for the coordinates of compounds in the visualization.

Singleton: a point with no neighboring points nearby. In the context of a distance horizon, any compound that has no other compound closer to it than the horizon is a singleton.

Tanimoto: similarity measure between two fingerprints, ranging from 0 (no similarity) to 1 (perfect similarity). It is computed as: 1-(#bits in common)/(#bits in either) A Tanimoto derived distance is computed as 1-Tanimoto.

Virtual library: a collection of compounds that exists only in computer representations. In this patent document virtual libraries more specifically refer to collections of all products that can be made by combining all suitable reagents in specific synthetic reactions, or to subsets of such products which meet additional criteria such as an upper bound on molecular weight.

Description

The problems of generating a two-dimensional display of high-dimensional diversity space involve the same type of considerations and limitations encountered with familiar geographic mapping. Accurately depicting points from a 1000 dimension space in two dimensions is impossible, as is preservation of distance/angle/area information when mapping the earth's curved surface onto the two dimensional plane of a piece of paper. For instance, a Mercator projection accurately maintains position and angular information but loses accurate area representation making high northern or southern land masses disproportionately large compared to mid-latitude areas. A homolosine projection on the other hand, preserves area relationships accurately, but loses other information.

The important point is that any two dimensional map preserve the feature/relationships critical to its particular use. In the present invention, the two dimensional maps preserve useful information about the distance relationships of compounds in diversity space. In particular, care is taken to preserve neighbor relationships by means of the horizon approach. A horizon is a distance beyond which all points are indistinguishable.

Just as an unaided eye cannot see objects obscured by the earth's curvature, the neighborhood principle asserts that when compounds are dissimilar enough, there is no information in quantifying that dissimilarity. Further, when molecular descriptors are employed which posses a neighborhood distance (validly relate descriptor space to biological properties), it is possible to relate biological activity distributions across the two dimensional plot.

The visualization method of this invention is based on two key ideas. First, large numbers of compounds can be represented by plotting only a subset of compounds that represent compact clusters. Second, the important information is contained in short range It distances between near neighbors. The preferred manner of practicing the method of this invention combines the sampling ability of the OptiSim methodology, standard PCA techniques of component projection, and a modified method of applying NLM with a modified stress function which uses the horizon to relax the mapping constraints. The methodology of the present invention is implemented in a computational environment where many programs may be used to display the scatter plots output by the projection and Java or other display environments may be used to display the results in an interactive manner. FIG. 1 shows the overall process:

Step A: Select the set of compound structures to be visualized. This may be one or more virtual libraries as well as one or more explicit libraries.

Step B: Compute a vector of molecular descriptors for each compound.

Step C: Generate a distance matrix between all compounds or utilize a function to generate the distance matrix elements as needed.

Step D: Compute a hierarchy of clusters, defining cluster centers and partitioning each set of compounds at each level. For small datasets this is not needed (equivalent to having each compound be alone in its cluster). For virtual libraries, which may contain millions of compounds, selection of representative subsets is both computationally necessary and a prerequisite for legibility of displays.

Step E: Perform a PCA projection onto the first two components. This provides an initial placement of compounds onto (x,y) coordinates. In the case of fingerprints, it also serves to spread out compounds in a useful way.

Step F: Run the NLM refinement of initial coordinates. The usual objective function in this algorithm has been modified for the current purposes to include a horizon limitation.

Step G: Create a graphical display from the coordinates of each compound. Do so such that the chemist can easily see which compounds are singletons 20 and can tell which set of compounds each point came from.

Additional Display—Step H:

If desired, features of the display environment could provide access to information useful to explore the points in the two dimensional plot. A display implemented in Java could service graphical inquiries such as:
1. How many compounds are represented by a specified cluster center compound?
2. How far apart are two compounds?
3. Where is this named compound in the graph?
4. What is the structure of this compound?
5. What is the nearest point to this compound in the "real" high dimensional space?

Possible additional Step I:

Subset Reprojection—Iterate to visualize subsets of the current graph, the purpose being:
1. To obtain more accurate depictions of a portion of the displayed diversity space.
2. To drill down into more detail by expanding selected cluster centers into all compounds that fall into the cluster partition.

Figure 2:
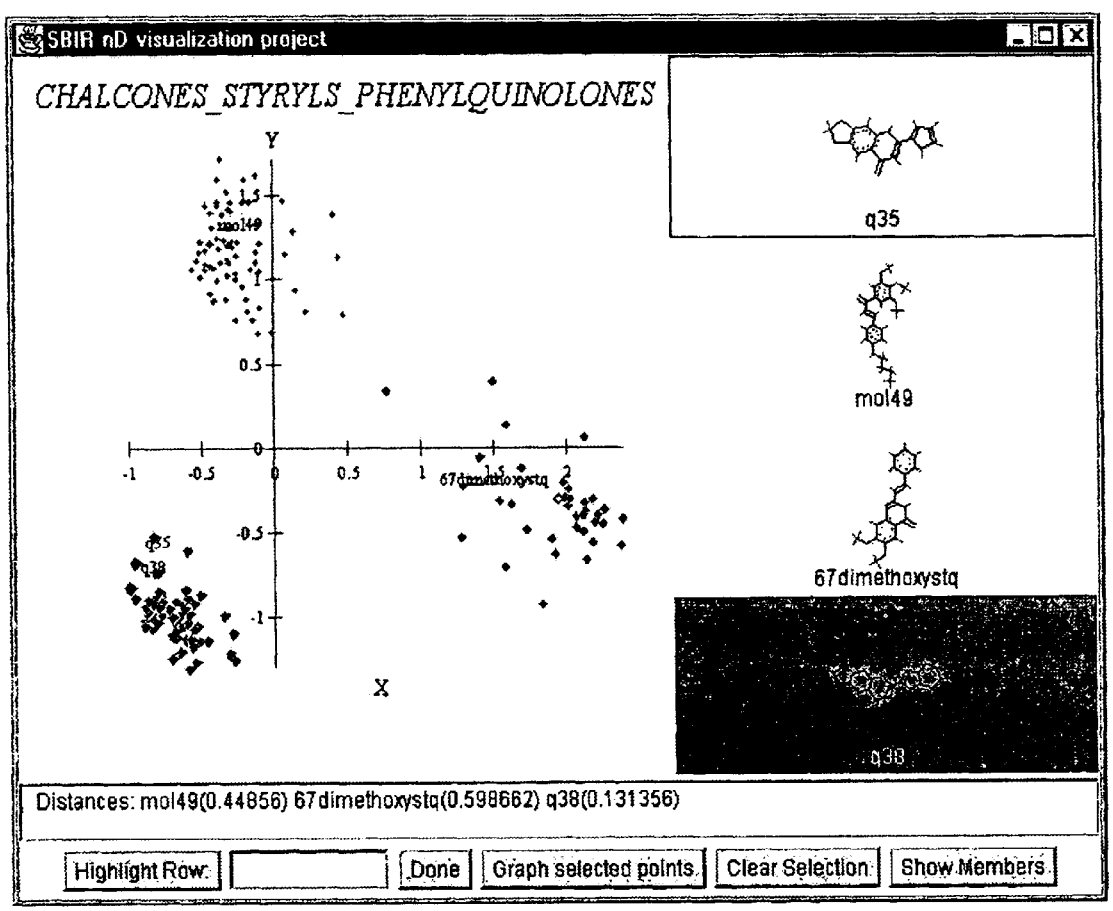
FIG. 2 shows a typical two dimensional projection using the method of the invention.

The process results in a display such as shown in FIG. 2. In this case the intent is to compare compounds which come from three distinct chemical series (chalcones, styryls, and phenylquinolones). The three series are divided into three clouds in the two dimensional projection. In this projection, the series are well separated. For this Figure, the chemist selected the compound q35 and requested that the nearest compound in each group be highlighted in the graph; the points mol49, 67dimethoxystq , and q38 are displayed as 2D structures in the right panels and the distance in the true fingerprint space from q35 to each is printed in the one line text window immediately below the graph.

As noted above, accurately depicting points from a 1000-D space in 2-D is impossible. We can achieve a useful level of success, however, by two related observations: we mostly care about preserving neighbor relationships, and we especially look for "overlap" of one set of compounds with another. The neighborhood issue has resulted in novel relaxation of mathematical constraints, while the overlap interest has led to novel biased selection methods from very large virtual library collections.

While it is believed that PCA/NLM has ever been used with fingerprints before, FIG. 2 also illustrates a critical difference between the visualization method of this invention and a "traditional" PCA/NLM type projection. The visualization method of this invention assumes that when two compounds are beyond each other's horizon—when they are far enough apart—then the exact distance between them is unimportant and need not be preserved. Specifically, it is most useful to run with a horizon of 0.30 in Tanimoto distance. Long range distances are ignored. This is evident in the graph where clusters appear to be separated by more than 1.0 units even though the largest possible Tanimoto distance is 1.0. So long as the compounds actually differ by 0.30 or more, there is not penalty for displaying them arbitrarily infinitely far apart.

Previous work by Patterson et al. revealed that when two compounds are more than 0.85 similar by the Tanimoto metric of fingerprint similarity (or at a distance of less than 0.15=1.0−0.85 in this graph) then they are likely to also show similar biological effects. At twice this distance, there is little or no predictive information about the activity of one compound to be obtained from knowing the biological activity of its partner.

In the original formulation of NLM (Sammon, 1969), the objective function to be minimized is the sum of squared fractional deviations between the distance matrix in the original high dimensional space and the distance matrix in the projected space: (True-Projected)/True. A small value is used in the denominator to avoid division by zero when necessary. In the modifications that have proven to work in the method of this invention, distances within the horizon are preserved:

Both "true" and "projected" distances are replaced with min(horizon, distance). This modification tends to make all truly close compounds look close in the projection. This is the minimal objective for the method: the structures should "look close if they really are close".

Thus a true distance of 0.35 and a distance in the 2D projection of 1.52 has a penalty of 0, since both true and projected are replaced with the same value, 0.30, yielding a fractional deviation of 0. However, a true distance of 0.30 with an apparent distance in the visualization of 0.03 has a relatively large fractional deviation of 90% and the NLM iterations will attempt to correct this after the true small distances are corrected. The usual NLM algorithm would spend its time trying to move the compounds which have true distances larger than 0.30 but apparent distances substantially larger. The principle modification of this method, imposing a horizon on distances of 0.30, does a good job in the short range while allowing large deviations to exist near and beyond the horizon.

As noted earlier, chemists are today faced with analyzing libraries which may contain millions of compounds. Clearly, graphical display of such vast number of data points in a meaningful way is impossible. For the purposes of this invention, generally only a few thousand data points at most can usefully be displayed on the screen. However, a representation of the distribution of the compounds in diversity space can be achieved by properly selecting compounds from the data set. The visualization graph of this invention is much like a geographical map. One does not expect to see a map of North America to show individual homes, or even every small town. As the map is narrowed to look at small regions such as a state or county, more detail is expected to appear in order to match the objectives of the viewer. Beyond 2000–5000 points the data obscure each other too much for productive use. It is not possible on most graphics screens to discern and select more than about 30,000 distinct points with uniform spacing. Since much information is in the holes as well as the points, the number of points suitable for display in any one graph is at most a few thousand. The limiting step for larger datasets is the partitioning of the compounds into one or more levels of clusters. Each level will contain a manageable number of points to graph.

The OptiSim method (Clark, 1997; Clark and Langton, 1998) is a method developed for the purpose of rapid clustering of large datasets. By varying key parameters, the selections can be made to vary from maximum dissimilarity, which is useful when the extreme edges of diversity space are of special interest, through complete linkage hierarchical clustering, which generates representative subsets. The OptiSim method is applied in the present invention primarily to generate subsets which are representative in the sense of partitioning the entire set of compounds into clusters of roughly equal volumes in the high dimensional space. However, the use of the OptiSim method can be varied according to which question is important at the moment: to see unexpected compounds which can be made from a specific reaction and available reagents, the maximum dissimilarity parameters are best.

To display a full combinatorial library, which typically consists of one billion similar structures, the library would be clustered on multiple levels with each point representing roughly 1000 structures on each level. The full visualization would then have the library at the top level with 1000 cluster centers, each one representing 1000 subcluster centers packed within the horizon, each containing about 1000 extremely similar compounds. The scientist would be able to see the overall distribution at the top level, could see much more detailed views of a part of the map when desired, and could go to a final level of individual compounds of the billion if appropriate. The zooming operation would be reasonably intuitive. Extension to multiple levels is straightforward and within the ability of a practitioner in the art.

Example Application of Method

The substructural fingerprints used in this example are binary vectors (bitsets) in which each element is set to 1 or 0 to indicate the presence or absence, respectively, of some substructural element in the corresponding molecular structure. The mapping is one-to-one for the substructure keys distributed by MDL,[1] whereas Daylight[2] fingerprints are hashed such that particular bits can be set by any of several different, unrelated substructures. UNITY®[3] fingerprints are qualitatively intermediate, in that only related substructures—e.g., alkyl fragments—get hashed together.

Fingerprints were originally developed to speed up 2D searches of chemical databases,[4] but recent work has made it clear that such fingerprints also work remarkably well for assessing similarities and differences between molecules in a biochemically meaningful way.[5,6,7,8,9] Because the bit string operations underlying their manipulation are very fast, fingerprints are particularly appealing as tools for dealing with the large amounts of data produced by the high throughput screening (HTS) and combinatorial chemistry programs currently underway at many pharmaceutical companies. In particular, one would like to present the relationship between sets of fingerprints in such a way that the full power of human pattern recognition can be brought to bear for elucidating structure-activity relationships (SARs).

Unfortunately, fingerprints do not lend themselves naturally to visualization, in part because of their high dimensionality. Indeed, it seems likely that their high dimensionality is directly related to their good neighborhood behavior—the fact that molecules with very similar fingerprints are very likely to exhibit similar biochemical properties.[7] There are simply too many ways for large numbers of compounds to be mutually distinct to be conveyed with complete accuracy in any low dimensional display space.

A second complication lies in the fact that the Euclidean distances to which people are accustomed are not the best way to measure distances in fingerprint space. This is because any particular substructure (e.g., a pyrazole ring) is much more relevant in terms of medicinal chemistry when it is found in one or both of two molecules than when it is absent from both. Hence distances (dissimilarities) between two fingerprints are more meaningfully assessed[10,11] using the Soergel[12] distance d given by:

$$d(a, b) = 1 - T(a, b) = \frac{\|a \cup b\| - \|a \cap b\|}{\|a \cup b\|} \quad \text{(Equation 1)}$$

where a and b are the fingerprints of interest, the double bars indicate cardinality, and T(a,b) is the Tanimoto similarity coefficient. Note that this distance measure runs from 0 to 1, and that bits which are set to 0 in both fingerprints do not contribute. Taken together, these considerations serve to reduce the effective dimensionality around each fingerprint, which helps to counteract the "curse of high dimensionality" referred to above.

According to Patterson et al.[7] and that of others,[5] two molecules separated by a Soergel distance of 0.15 or less (corresponding to a Tanimoto similarity coefficient of 0.85 or more) are likely to exhibit biological activities within two orders of magnitude of each other, which makes them substantially redundant in terms of HTS. Hence, 0.15 is generally used as an exclusion radius when selecting subsets from a combinatorial library.

Example Methodology: The Sulfonylpiperidine Urea Library

Figure 3:
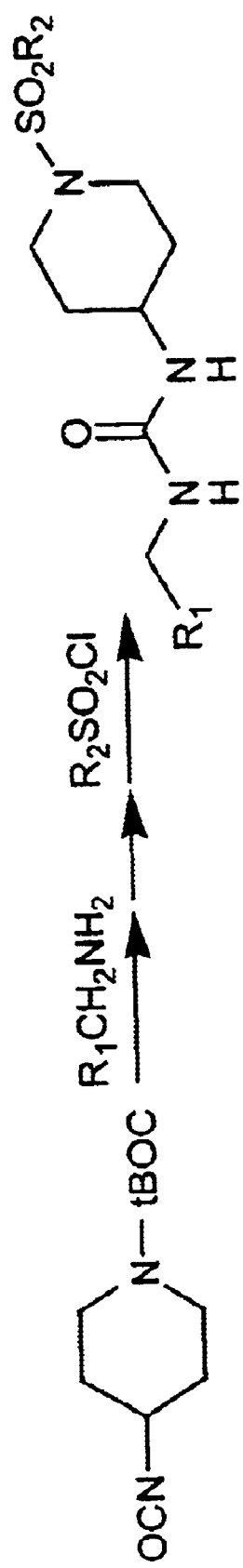
FIG. 3 shows the virtual reaction which defining the sulfonylpiperidine urea combinatorial library.

Consider, for example, the virtual library defined by the reaction shown in FIG. 3, which could be used as a platform from which to design generic screening sub-libraries. The 4-aminopiperidine scaffold upon which the full library is built is not commercially available, but it is a known compound. A UNITY substructure search of commercially available reagents was run and the candidate reagents obtained were screened in ChemEnlighten[14] for desirable physical properties.

UNITY 2D searches were restricted to molecules containing no more than ten rotatable bonds, and reagents containing the substructural fragments listed in Table 1 were excluded by using the —notlist option in dbsearch. Note that a moderate level of potentially interfering functionality (e.g., single free hydroxyl groups) was permitted, the assumption being that a modest investment in protection and de-protection chemistry could be accommodated. The primary amine and sulfonyl chloride hitlists obtained were then loaded into ChemEnlighten databases and filtered for the physical property limits listed in Table 2. A total of 308 distinct primary amines passed the filters, as did 154 sulfonyl chlorides, so the full library encompassed 47,432 products.

The filters applied were chosen with an eye towards generating products with generally drug-like properties,[15] and succeeded reasonably well −91% of the products in the resulting library had a molecular weight less than or equal to 550 (68% less than or equal 500), and 95% returned a CLogP of 5.0 or less. Most contained one or two aromatic rings (38 and 46%, respectively).

Additional filters are, of course, involved in creating "real" libraries, but those used here are stringent enough to ensure that the distribution of substructural features in the resulting library is realistic. In addition, they produce a range of products which illustrate the behavior of visualization methods at hand. The product library is also realistic in that it is flexible enough to explore an interesting range of binding site geometries, but not so flexible that tight binding is likely to be precluded by the entropic cost of "freezing out" rotatable bonds.

OptiSim Subsets

It is not necessary to project data points for all 47,432 products from fingerprint space simultaneously to get a good idea of the various structural relationships which exist between the compounds which make up the library. Indeed, it is impossible to fully resolve that many points even in three dimensions, let alone in the two dimensions to which one is restricted on a computer screen or in print. Instead, a subset can be selected in such a way that it is representative of those compounds not shown, and which provides a useful mechanism for "drilling down" to any required level of resolution.

This can be accomplished by examining a random sample, which is, indeed, quite efficient if the structures are uniformly distributed or if one is looking at more than 10 or 20% of all the compounds in a given data set. Unfortunately, combinatorial libraries are often rather unevenly distributed across the region of fingerprint space spanned by each, in that distances between clusters of related products vary depending on the relative structural complexity of the substituents (alkyl vs phenyl vs azoles) and the nature of their linkage to the combinatorial core, as does the "density" of each cluster. Hence a random sample large enough to cover the space adequately tends to produce at least one area where the point density is too high to be useful for evaluating the co-localization and segregation of, for example, activity classes.

Subsets obtained by applying the OptiSim methodology[17,18,19] to a large library are more informative, however, in that they are representative enough to give a good sense of the distribution of structures within a library, yet diverse enough to accurately convey its coverage of the available structural space. Such selection sets are built up by pulling the best representative from a series of candidate subsamples and adding it to the set of compounds already selected. Subsample sizes k of 3 to 5 generally work well, so creating selection sets is very fast. Using OptiSim selection is also convenient in that the library need not be fully enumerated: selection can instead be made directly from a combinatorial definition—e.g., from a combinatorial SLN[20] (CSLN in SYBYL Line Notation).

An initial subset of 300 compounds was drawn from the sulfonylpiperidine urea library by running OptiSim with an exclusion radius (distance below which compounds are considered redundant) of 0.15 and a subsample size k=3. Working from a subset has the side benefit of reducing the effective dimensionality of the problem to a considerable degree, since the underlying level of dimensional complexity is always less than the number of compounds being examined. In this example, that translates to a potential reduction from 988 dimensions (the number of bits in a standard UNITY fingerprint) to 300 or less.

Combinatorial Sub-libraries

Briefly described below is an example of how a combinatorial sub-library could be selected for ultimate use with the method of this invention. The method of comparing combinatorial sub-libraries using the two dimensional projections implemented by the method of this invention will be described later in this patent document.

Figure 4:
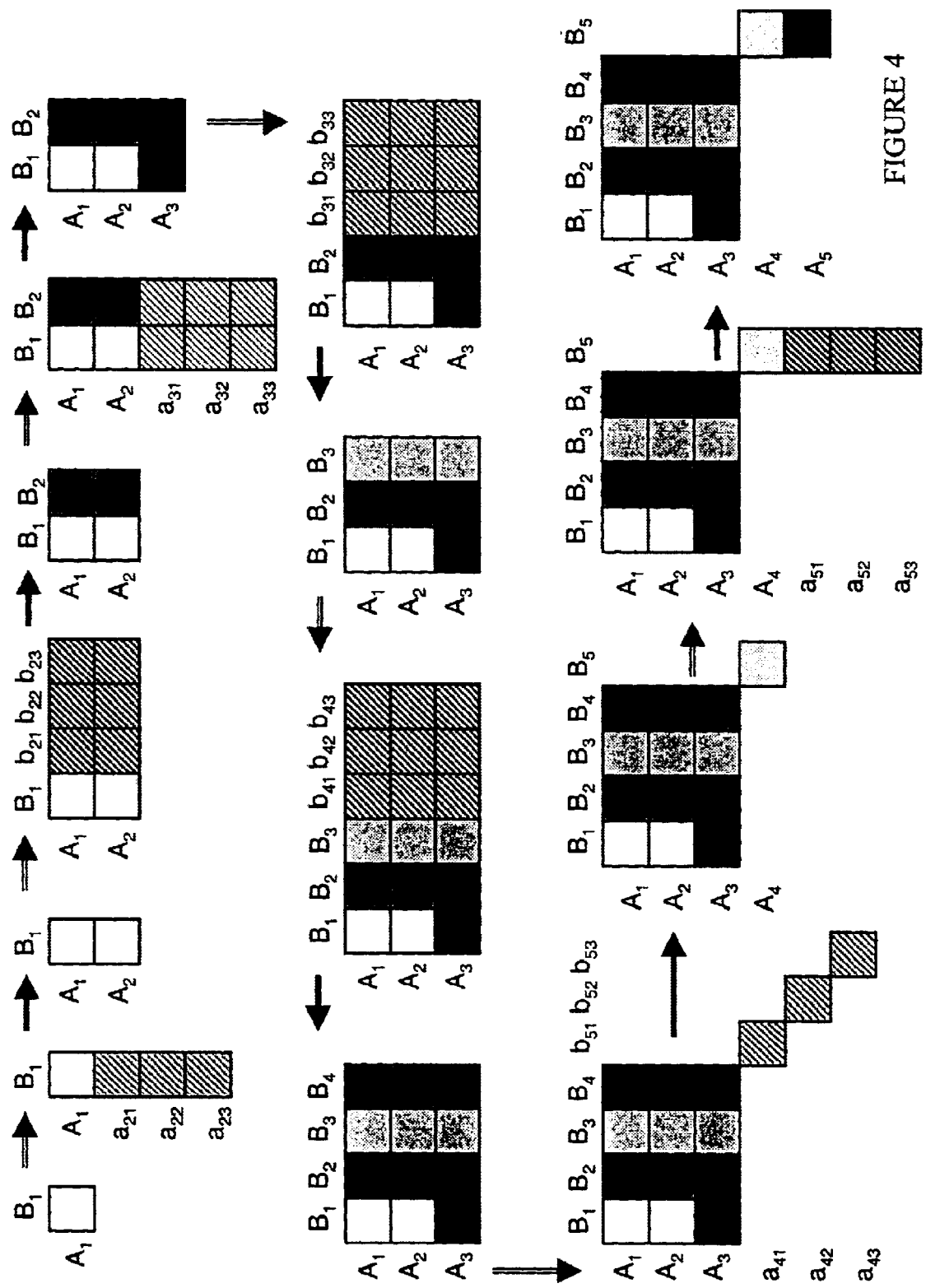
FIG. 4 is a schematic illustrating the application of OptiSim methodology to combinatorial sub-library design for a two-component reaction defined by A+B →AB. Upper case letters correspond to selected reagents; lower-case letters denote candidate reagents in subsamples considered at each step, with cells shaded to indicate the order in which products are added to the design. Block dimensions are set at 3×4 and k is set to 3 for illustrative purposes.

Combinatorial sub-libraries were generated by applying the OptiSim[17] extension illustrated in FIG. 4. The process is seeded by choosing one product at random, which specifies the first reagent pair $A_1B_1$. At each step, new reagents are chosen at random from the list of those available and the products produced from each by reaction with the complementary reagents which have already been specified are examined. That reagent whose products compare most favorably to the sub-library which has been built up so far are added to the selection list for the appropriate reagent. What exactly "most favorable" means is very flexible; it may simply mean most diverse, but can also involve considerations of cost or synthetic compatibility.

In FIG. 4, the subsample size k is set to 3 for illustrative purposes, and a 3×4 pattern has been specified. Compound $A_1B_1$ is selected at random to seed the process. Reagent candidates $a_{21}, a_{22}$ and $a_{23}$ are then considered by comparing $a_{21}B_1, a_{22}B_1$ and $a_{23}B_1$ to $A_1B_1$. That candidate which produces the best set of products (most diverse, cheapest, best average expected activity, etc.) specifies $A_2$. In the next step, three candidate reagents B are selected: $b_{21}, b_{22}$ and $b_{23}$. Each candidate will now give rise to two products—$A_1b_{2i}$ and $A_2b_{2i}$—which get evaluated against $A_1B_1$ and $A_2B_1$.

Selections from the reagent lists alternate until one of the specified block dimensions is reached; the corresponding reagent is then skipped over until the full block is filled out. Once a block is completed, a new seed is chosen by picking k candidate compounds at random and comparing them to the products in the blocks which have already been specified. The process then continues as for the first block until the required number of products have been specified or no valid selections remain.

Note that no products from reactants selected for earlier blocks are considered in selecting the seed product (e.g., $A_4B_5$ in FIG. 2) which starts a new block, and that all products in preceding blocks are considered when evaluating candidates for subsequent blocks. In FIG. 4, for example, similarity of $a_{42}B_5$ to $A_2B_3$ may militate against the selection of $a_{42}$ as $A_4$.

Three 200 member sub-libraries were created using a combination of customized code in SYBYL[21] Programming Language (SPL) and commercially available functions from the Legion™ combinatorial builder module of SYBYL. The value of k was set to 5 and block dimensions were set to 1×1 ("cherry picking," which is identical to ordinary OptiSim selection), 10×5 ("four blocks") or 20×10 ("single block") for primary amines and sulfonyl chlorides, respectively.

Reagent subsamples were chosen at random with uniform probability from among those for which no anticipated product fell within an exclusion radius of 0.10 of any product already specified. Candidate reagents were selected with replacement, and so could be selected for inclusion in several different blocks. In fact, only 32 primary amines are called for in the "four blocks" design, because four contributed to two different blocks and three appeared in three blocks. No sulfonyl chlorides were used more than once, so the design would require a total of 52 reagents versus the 30 used in the single block design.

Roulette wheel selection weighted by price, supplier, etc. can easily be incorporated into the subsample selection process, as can categorical exclusion criteria such as physical property cutoffs ("druggability").[15]

For the libraries described here, candidate reagents were rated simply on the basis of diversity. In particular, the MiniMax criterion was used to select the best candidate at each stage: that reagent was selected for which the maximum Tanimoto similarity to any already-specified product was smallest. Other metrics (e.g., smallest average cosine coefficient) can be used in place of MiniMax Tanimoto, and non-structural criteria can be incorporated into the fitness function if desired.

A thorough characterization of the library designs obtained using OptiSim in this way is beyond the scope of this patent document, but several salient points bear mentioning:

Replacement of "bad" reagents which slip past the filters simply entails re-running the corresponding step in the analysis while including products specified at subsequent steps when evaluating replacement candidates; replacing $B_4$, for example, would involve comparison of its products with $A_5B_8$, $A_{10}B_4$, etc. as well as with $A_1B_1$ and $A_3B_2$.

Extension to reactions involving more than two reagents is straightforward.

Perhaps most interesting is the use of roulette wheel selection in place of uniform random sampling for choosing subsample candidates. Introducing a particular bias (e.g., towards cheaper reagents) when deciding which subsample of reagents to consider next can produce quite different results from those produced by adding analogous terms to the fitness function used to select the "best" candidate from each subsample.

Note that sublibraries obtained in this way are both representative and diverse, in the same sense that OptiSim selection sets are.[18,19] For any given block layout, the balance between the two characteristics is set by the value chosen for k: smaller subsample sizes give more representative sublibraries and larger subsample sizes give more diverse ones.

PCA and NLM Projections

Figure 5A:
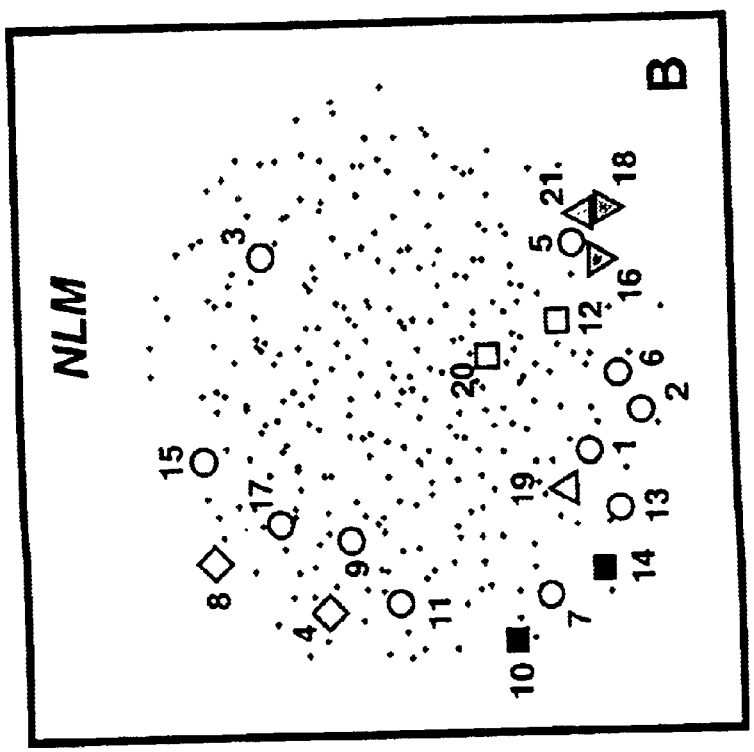
FIG. 5 shows projections of fingerprints for a 300 compound OptiSim subset (k=3) of the sulfonylpiperidine urea into two dimensions. Paired symbols indicate more closely related compounds, whereas circles correspond to relatively isolated ones. Structures for compounds represented by highlighted points are given in FIG. 5. (A) Map based on scores from the first two components of a principal components analysis (PCA) using Euclidean distances between fingerprints. (B) Non-linear map obtained from the coordinates in (A) using Soergel distances and the stress function given in Equation 2.

Principal components analysis (PCA) has seen extensive use in diversity analysis.[23,24] FIG. 5A shows the projection obtained by extracting the first two principal components from the fingerprint space for the 300-compound OptiSim selection set described above. This subset includes eleven compounds which have no neighbors within a Soergel radius of 0.3, beyond which biochemical similarity falls off rapidly; their positions in the plot are highlighted as open circles. It is not at all obvious by inspection of the principal components projection that these eleven compounds are structurally isolated. In fact, they all tend to fall into the central areas of the map.

Figure 6:
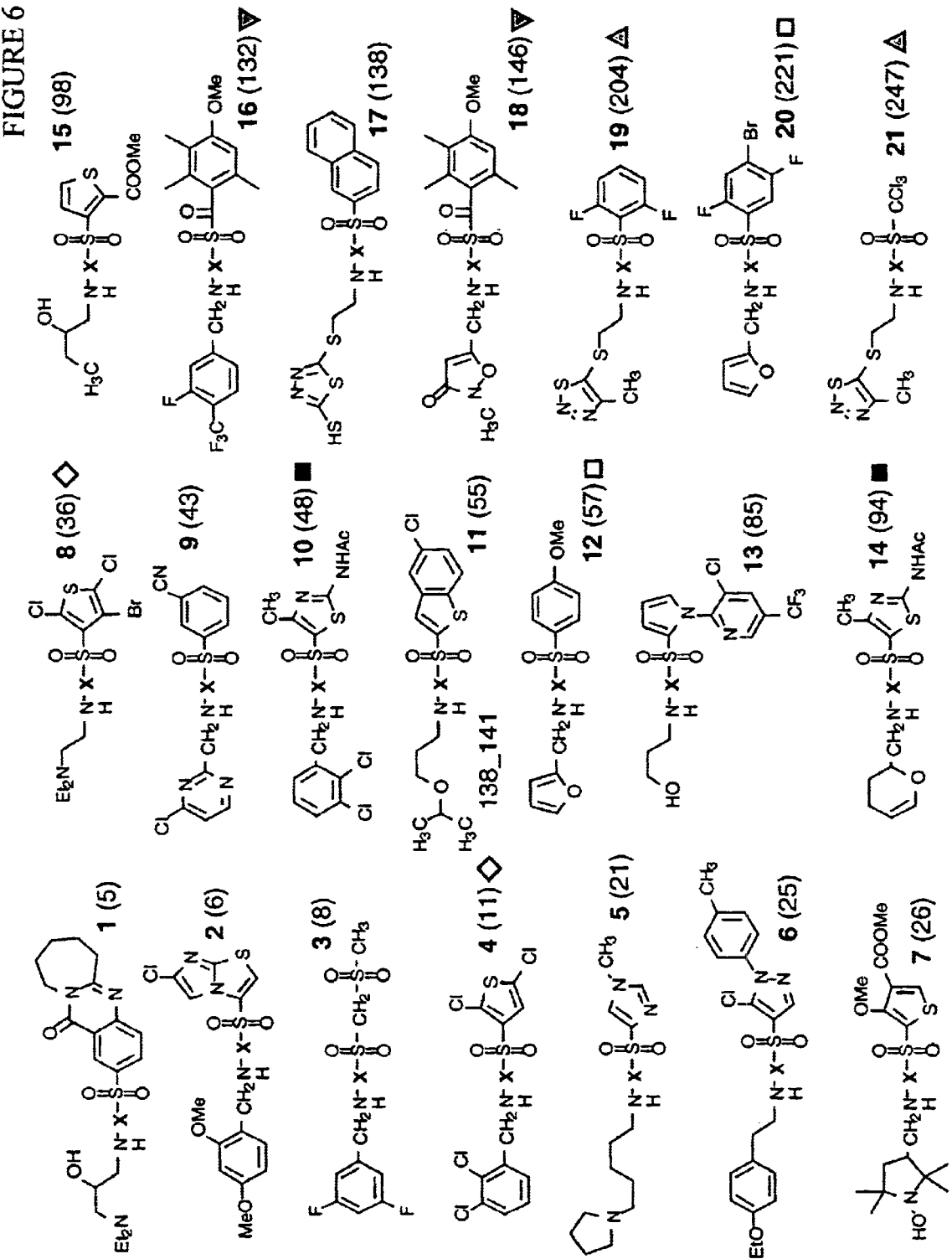
FIG. 6 shows structures for the particular sulfonylpiperidine ureas highlighted in FIGS. 4 and 5. Numbers in parentheses indicate the OptiSim selection index for each product. X denotes the piperidyl core.
Figure 7B:
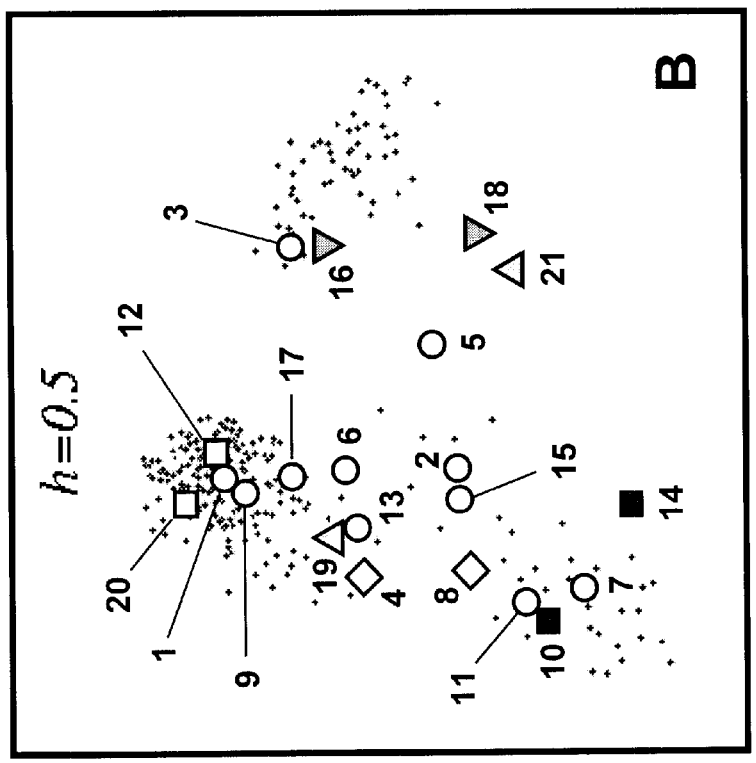
FIG. 7 shows non-linear maps for the 300 compound OptiSim subset. Initial coordinates obtained from PCA were relaxed by minimizing the modified stress function given in Equation 3. Highlighted points refer to the structures shown in FIG. 3. (A) h=0.65. (B) h=0.5. (C) h=0.4. (D) h=0.3.
Figure 7A:
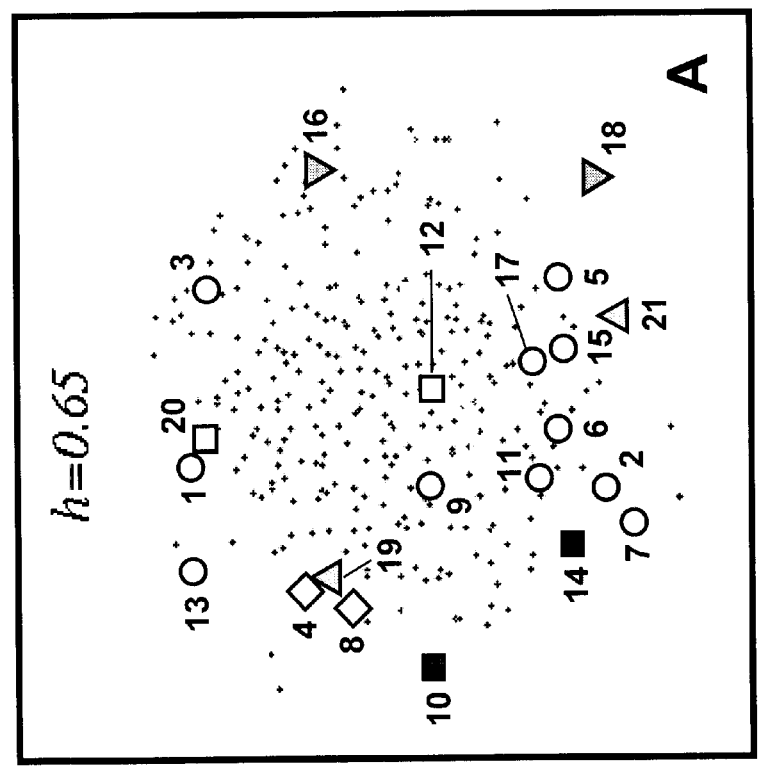
Figure 7D:
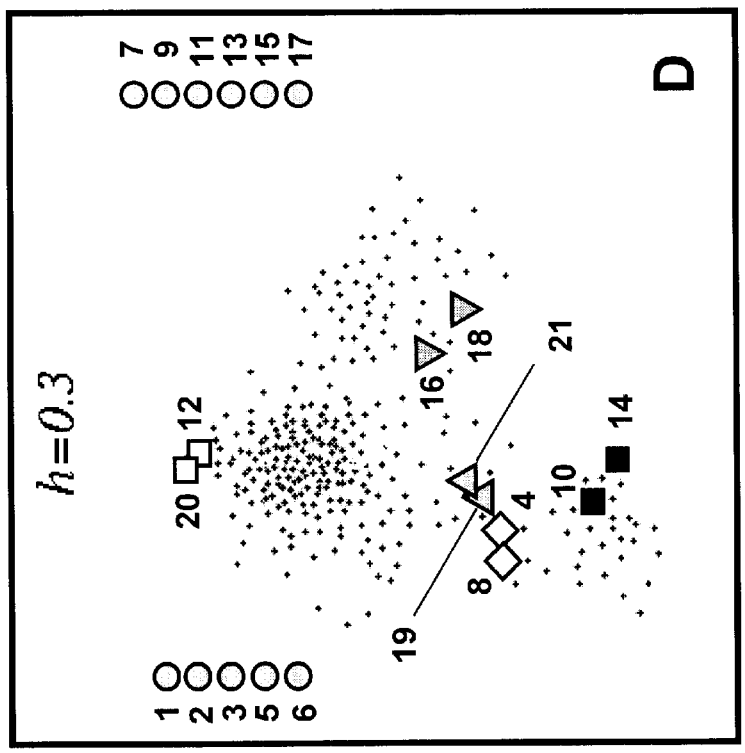
Figure 7C:
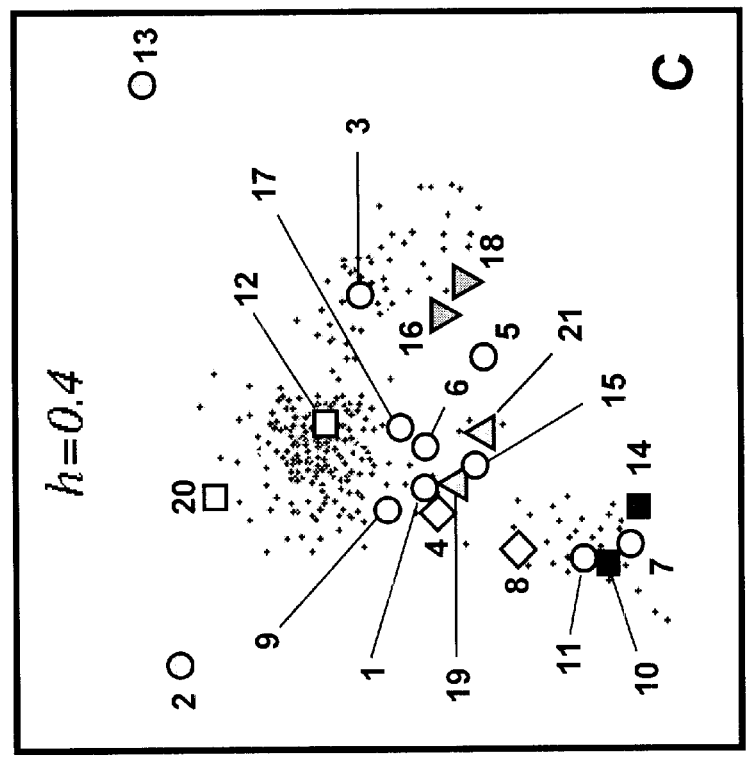

FIG. 6 includes the corresponding structures, which are numbered in parentheses in the order in which they were brought into the OptiSim selection set; "X" in each chemical structure denotes the shared piperidine core.

Figure 5B:
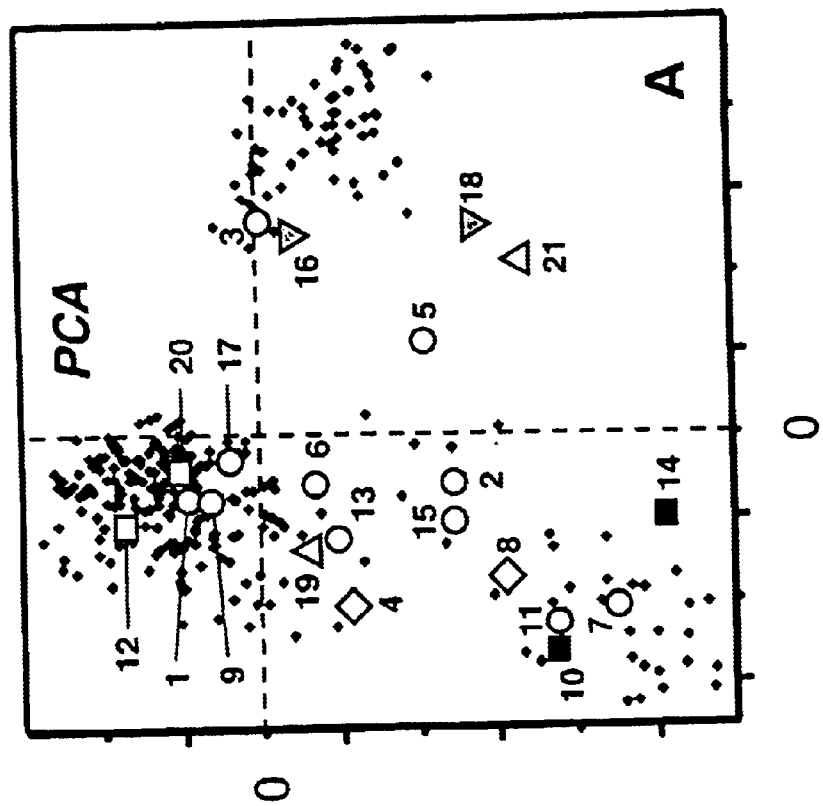

The PCA map can be modified to better reflect the real pairwise distances within the data set by applying a non-linear mapping technique (NLM) developed originally by Sammon[25] and subsequently extended by Kowalski and Bender[6] and by others.[27,28,29] In this approach, the PCA coordinates are perturbed so as to minimize some stress function. FIG. 5B shows the result of doing this for the sulfonylpiperidine ureas using Sammon's original stress function S:

$$S = \sum_i \sum_{j>i} \frac{(d_{ij}^* - d_{ij})^2}{d_{ij}} \qquad \text{(Equation 2)}$$

where $d_{ij}^*$ is the distance between points i and j in the projection, and $d_{ij}$ is the distance between i and j in the original space. Here, we are interested in the Soergel distance.

The isolated points have been displaced towards the edge of the map, which is clearly desirable. This improvement comes, however, at the cost of reducing the anisotropy of the map—the distinctive shape of a PCA projection is characteristically reduced or lost altogether in generating a non-linear map from a high-dimensional space, particularly for data sets as inherently symmetrical as combinatorial libraries.

Many near neighbors in the fingerprint space are also near neighbors in both projections (not shown), but many have been pulled apart in the PCA or the NLM projection, or in both. Examples include the other ten compounds highlighted in FIG. 5A and 5B, which have been paired up by similarity; their structures are also shown in FIG. 6. The Soergel distances separating 12 from 20, 10 from 14, 19 from 21, 4 from 8, and 16 from 18 are 0.243, 0.249, 0.271, 0.304 and 0.339, respectively. These separations are small enough to imply a substantial potential for similarity in biological activity but large enough that differences in potency can be expected to exceed 100-fold. Such pairs form the bridges which link structural islands of biological activity, so getting an accurate presentation of their relationship to each other is critically important.

A Modified NLM

Unfortunately, the relatively large separations which dominate the NLM in FIG. 5B are precisely those which carry the least amount of useful information; it is the local similarity which matters most. Once the Soergel distance between two fingerprints gets much beyond 0.4, one can conclude that the corresponding structures are different, but not really how different they are.[30]

This consideration has been incorporated into the NLM in the method of this invention by modifying the stress function so that each compound only "sees" compounds which lie within a neighborhood of radius h around it. This has been accomplished by replacing each of the distance terms in the numerator of Equation 2 with the distance h to the horizon whenever two compounds are far apart (Equation 3).

$$S = \sum_i \sum_{j>i} \frac{(\min(h, d_{ij}^*) - \min(h, d_{ij}))^2}{d_{ij}} \qquad \text{(Equation 3)}$$

Sacrificing long-range interactions in this way allows the NLM to relieve stress by unfolding. This is illustrated in the displays of FIG. 7, which shows NLM plots created by minimizing the modified stress function defined in Equation 3 as h is reduced from 0.65 down to 0.3. Compounds which do not fall within the horizon of any other compound in the subset being examined cannot be placed meaningfully into the projection and so are set off to the edge of the plot (shaded circles in FIG. 7C and 7D). Two compounds—2 and 13—are excluded at h=0.4 (FIG. 7C) but compounds 12 and 20 remain well-separated, as, to a lesser extent, do compounds 4 and 8. Upon contracting the horizon still further to h=0.3, the remaining nine isolated compounds are pushed off the map, whereas all five problem pairs cluster appropriately.

Figure 8:
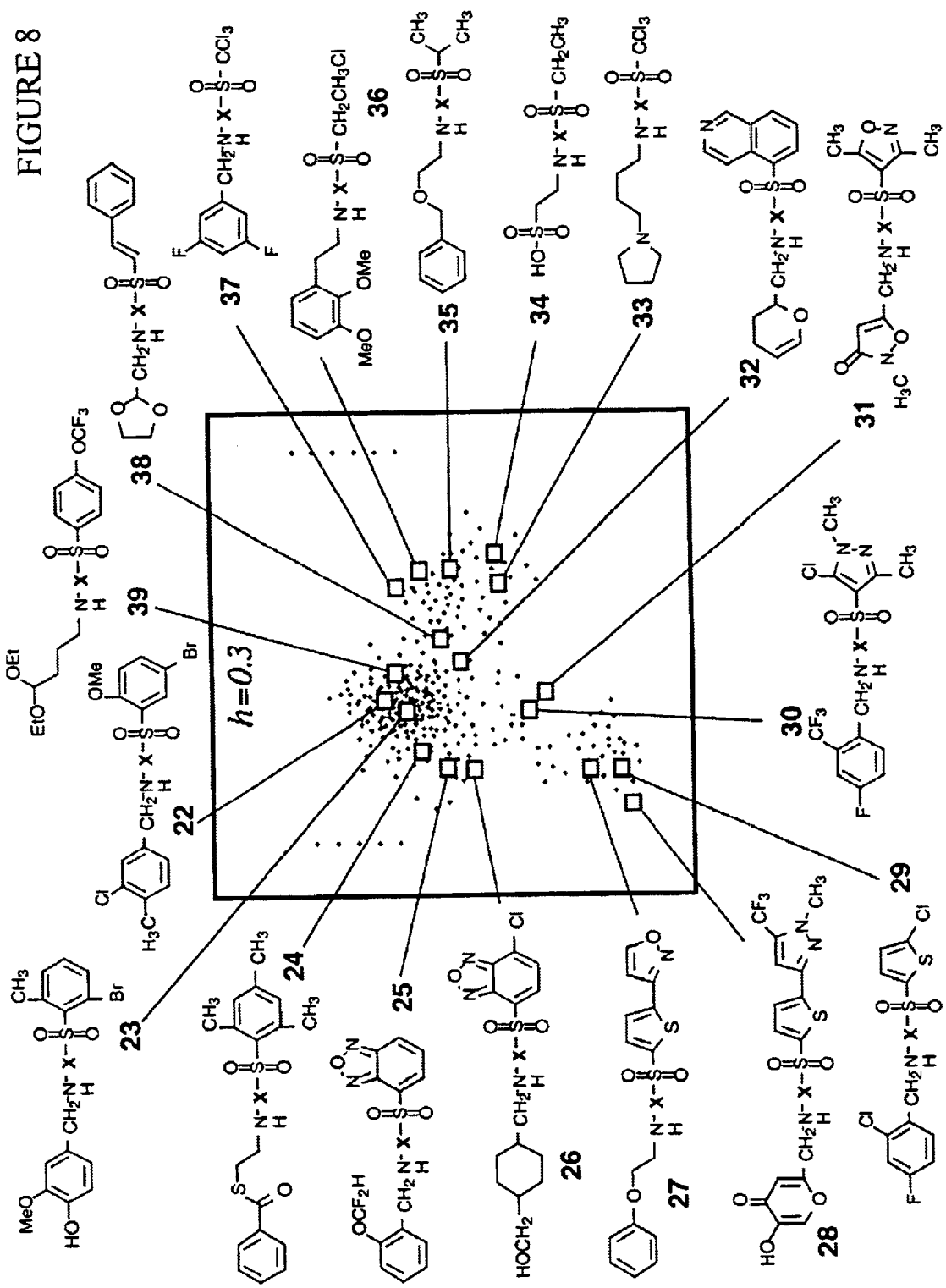
FIG. 8 shows a Non-linear map for the 300 compound OptiSim subset obtained with h=0.3. Highlighted products were selected to illustrate the relative distribution of structural classes across the map.

The acid test for any visualization method is its ability to order structures in a way which makes sense to a medicinal chemist. FIG. 8 again shows the projection for the 300 compound OptiSim selection set at h=0.3, but with different compounds highlighted to illustrate the rather "natural" layout of substructures produced by the introduction of an horizon.

As one might expect from the chemistry involved in production of the respective reagents, benzenesulfonyl chlorides and benzylamines dominate the pools of available reagents. Their mutual prevalence is reflected in the dense clump of diaryl compounds (e.g., 22 and 23) in the upper left quadrant. Those rare compounds such as 3 and 34, which lack aryl groups altogether, co-segregate in the sparsely populated area to the right of center in the map, whereas alkylamino arylsulfonamides 26, 32, 38 and 39 occupy the center and center left. Arylamino alkanesulfonamides 35–37 fall into the upper right quadrant, with the more aliphatic 35 positioned towards the bottom of the cluster, near the non-aryl 33 and 34. Thiophenes and azoles (e.g., 27–31) appear in the lower left quadrant. Compound 28 is a particularly distinctive compound and so shows up at the periphery of the plot, near the less unusual 5-isoxazolylthiophene-2-sulfonamide 27. The "reasonableness" of such distributions, which is intuitively appealing to medicinal chemists but which in the past has been difficult or impossible to quantify, now has a firm analytical footing in the vizualization method of this invention.

Comparing Combinatorial Sub-libraries

Figure 9A:
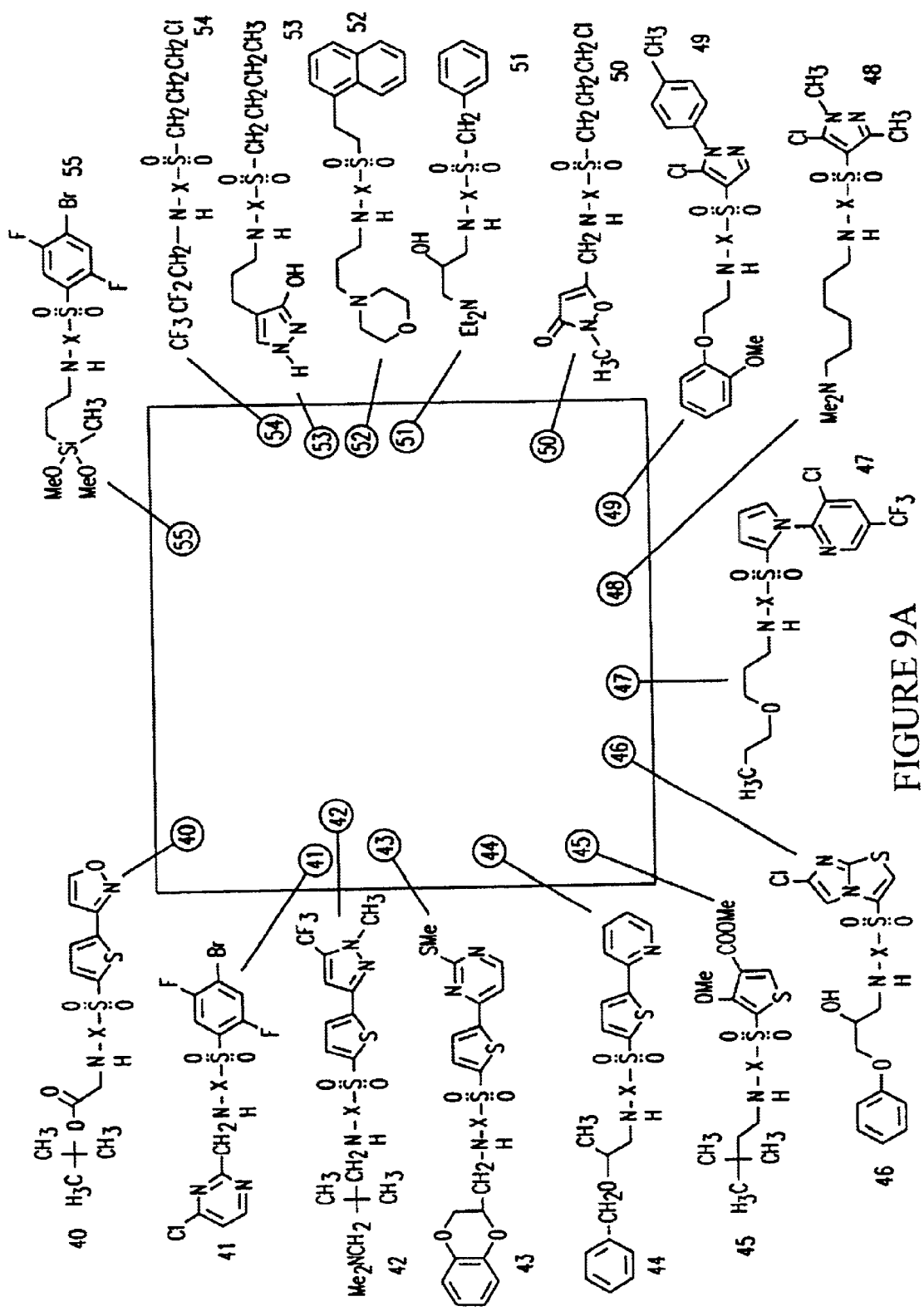
FIGS. 9A and 9B show a non-linear map for combinatorial sulfonylpiperidine urea sub-libraries. Each sub-library was comprised of 200 products, of which 100 were chosen at random and projected together using h=0.3. "Cherry picking" indicates OptiSim selection, whereas single- and four-block designs were created using an extension of OptiSim described in the text. A subsample size k=5 was used in generating each of the three designs.
Figure 9B:
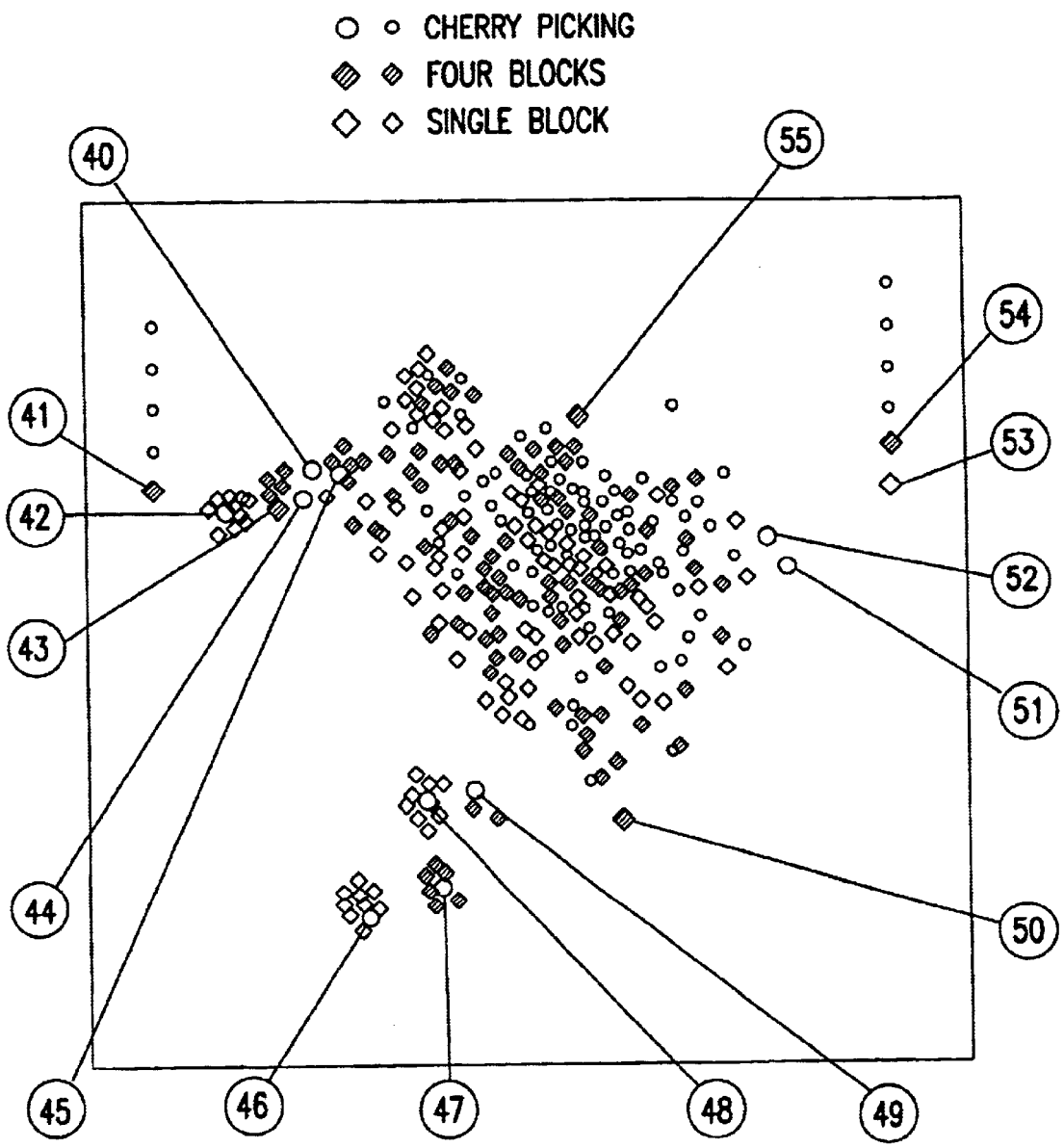

Relationships among two or more libraries are best visualized by projecting them into a common NLM, but using fingerprints from all 600 compounds in the individually selected, four block and single block sub-libraries described above produces an unnecessarily overcrowded map. Instead, 100 compounds were drawn at random from each sub-library. The three samples obtained were then pooled, and projected together using h=0.3 to create the map shown in FIG. 9.

This plot clearly supports the expected conclusion[32] that the sub-library of individually selected compounds (cherry picking design) is the most diverse, whereas the single block design is the least diverse and, concomitantly, the most redundant. One indication of this is the eight representatives from the cherry picking library which appear along the edge of the plot, indicating that they fall beyond the horizon of any other compound in the sub-libraries. By contrast, only two such outliers (41 and 54) were produced by the four block design, and only one (53) by the single block sub-library. In addition, the individually selected compounds are clearly more evenly spread in general. Finally, note the redundancy indicated by the large clumps of single block compounds which surround 42, 46 and 48.

These points could probably be gleaned from summary statistics calculated "blind" using pairwise distances or other numerical data. However, such analysis would not detect the significant under-sampling of compounds evident in the upper right quadrant circumscribed by 51, 52 and 55, particularly in the single block design (large green symbols). The ability to identify such diversity "holes" by direct inspection is a major advance enabled by the present invention.

Visual comparisons of such projections also provide a way to assess trade-offs in optimality among factors such as coverage, diversity, synthetic efficiency, cost and redundancy across variations in sublibrary design parameters (e.g., subsample size k in the OptiSim design strategy described here).

Projecting Biological Activity into Fingerprint Space

Figure 10B:
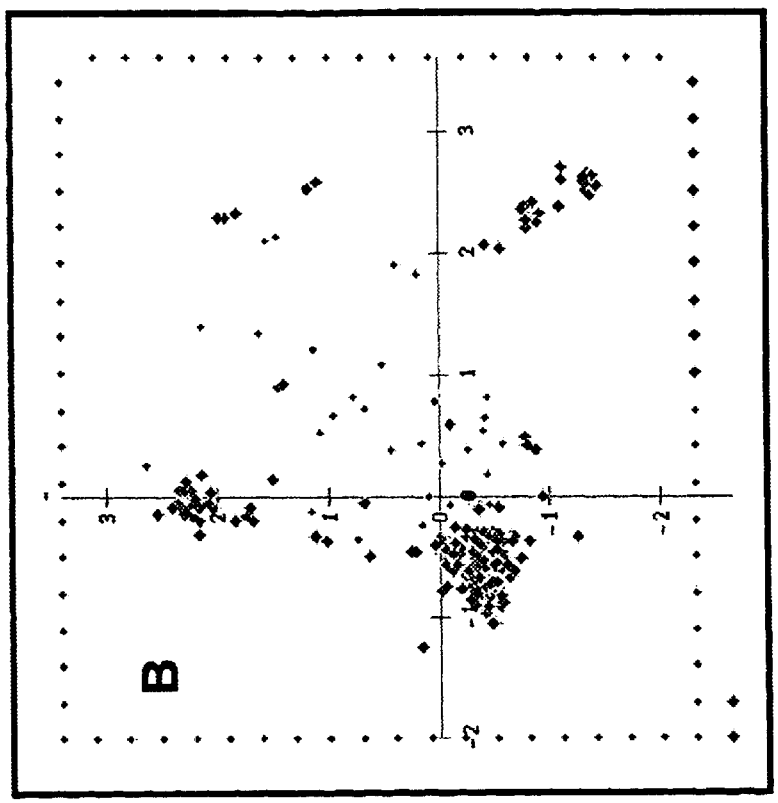
FIG. 10 shows non-linear maps showing projections of biological activity and pharmacophoric structure into fingerprint space for a proprietary library of potential kinase inhibitors with respect to a specific kinase target. Large symbols indicate actives, whereas small symbols denote generic inhibitors which failed to inhibit the target enzyme. Specific actives are highlighted as circles and squares. (A) PCA map for 100 actives selected at random together with 300 randomly selected inactives. (B) "Classical" NLM (h=1.0) obtained starting from the PCA coordinates in A. (C) Modified NLM obtained using an horizon h=0.3. (D) Map for actives and inactives "hit" in a UNITY 3D flex search run against a query built from a particular pharmacophore model of the target enzyme's active site.
Figure 10A:
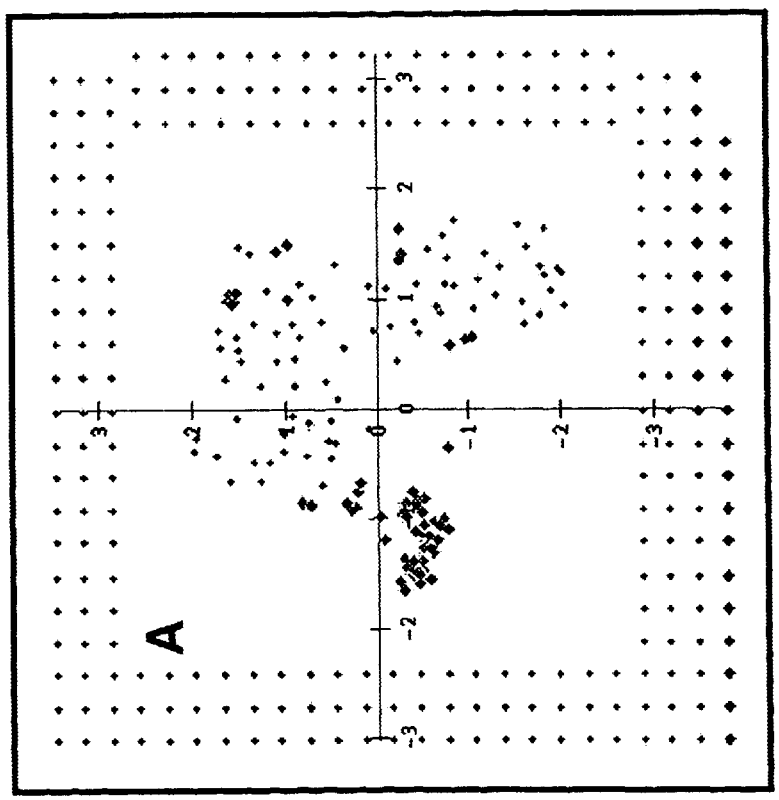
Figure 10D:
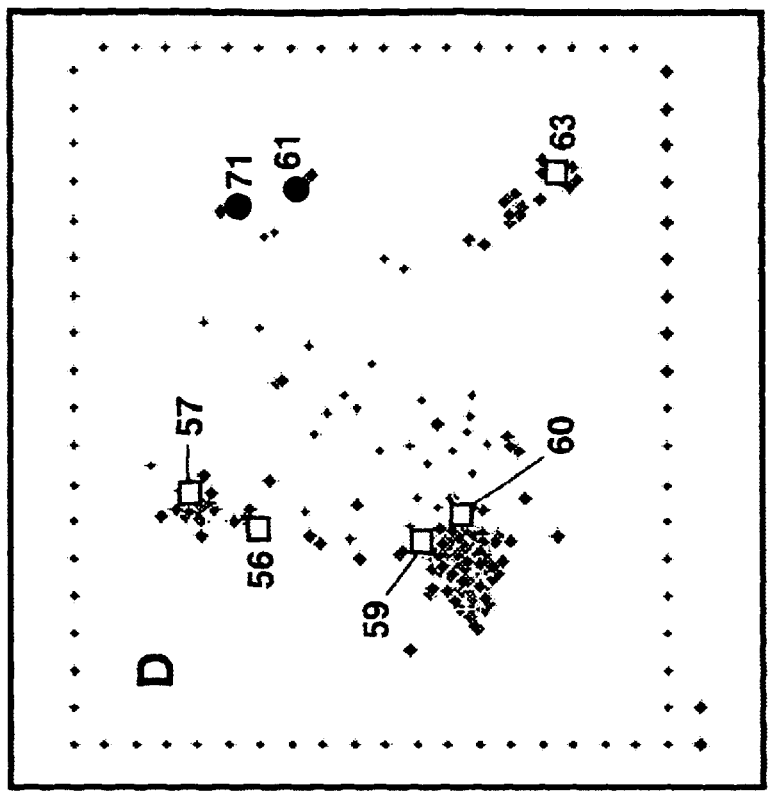
Figure 10C:
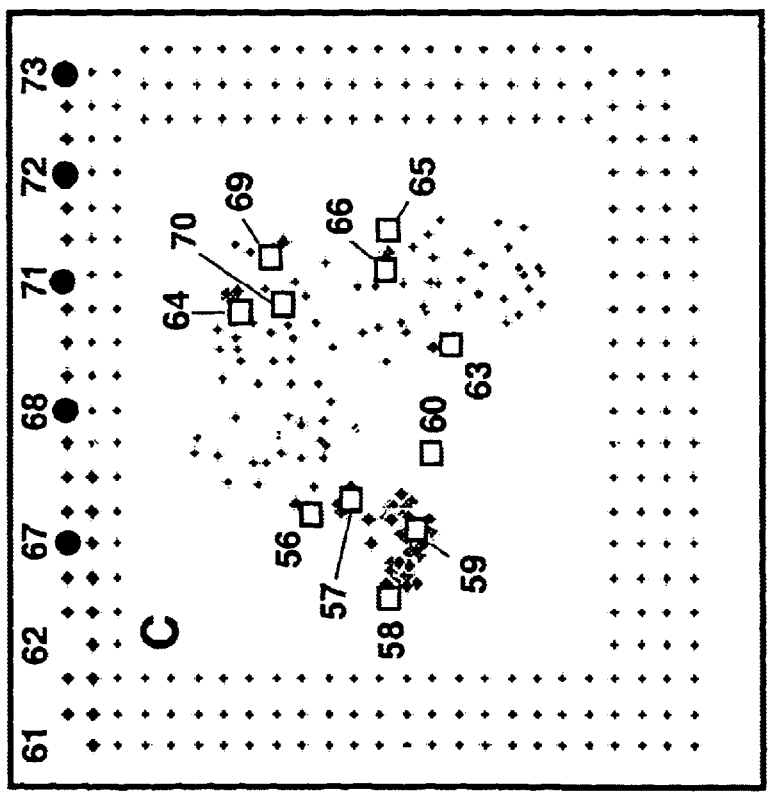

Analyses carried out on literature data sets have clearly shown that 2D fingerprints exhibit good neighborhood behavior.[7] The visualization method of this invention provides a less abstract demonstration of this point. To accomplish this, we examined the results of assaying a generalized screening library of proprietary kinase inhibitors against a specific target enzyme, then applying the combination of PCA and modified NLM projection to fingerprints for 300 compounds drawn at random from the pool of inactives together with 100 randomly selected actives. The plots obtained are shown in FIG. 10A–C, with actives indicated by larger symbols and inactives by the smaller symbols. FIGS. 10A and 10B show the PCA and direct (no horizon) NLM projections for this data set, whereas the plot in FIG. 10C was obtained with h=0.3.

There is much more structural diversity among compounds in the kinase data set than is found in the sulfonylpiperidine library, with 80% of the pairwise distances between the fingerprints from the kinase library in excess of the maximum pairwise separation (0.714) seen in the combinatorial one. The large number of long-range interactions involved reduces the extent of "rounding up" possible in this case when going from the principal components projection (FIG. 10A) to unmodified NLM (FIG. 10B).

A handful of inactive compounds fall into the cluster of actives which includes compounds 56–60, and 70 and 71 are juxtaposed in both FIG. 10A or FIG. 10B despite the large pairwise separation between them (0.861) in fingerprint space. Applying our modified NLM procedure with h=0.3 (FIG. 10C) removes 61, 62, 71 and other outliers—i.e., compounds with no neighbors within a Soergel distance of 0.3—into the frame of the plot and purges the inactives from the large cluster of actives to the left of the plots. Moreover, the stress drops from 9034 to 36 in going from FIG. 10B to 10C. Other compounds have been highlighted as light blue squares to illustrate how imposing the horizon affects their distribution relative to one another. A greater proportion of inactives (56%) show up as outliers in FIG. 10C than is the case for the actives (30%), indicating that the distribution of "hits" is gratifyingly non-random. Of greater interest, however, are the several islands of activity set off from one another by intervening stretches of inactives: good neighborhood behavior implies that such islands will be relatively free of inactives, though it does not preclude the existence of multiple islands. Nor does it imply that the scale of coupling between activity and structure will be the same everywhere. Indeed, some of the "shorelines" in FIG. 10C are much more sharply defined than others. Cases in which structural changes as simple as adding a methyl group produce a dramatic drop or increase in biological activity represent extreme instances of this, but they in no way disprove the existence of the islands themselves or the continuity of the activity—and lack thereof—on either side of such boundaries.

Direct examination of the underlying structures shows that each island represents a more or less different chemical family from the large island at the left of the plot, particularly for those farther afield. Some of the compounds which make up the smaller islands are quite active and so may represent new lead areas of chemistry ripe for more thorough exploration.

The inactive compounds make a key contribution to this plot by defining the "shores" of the islands of activity. Note, in fact, that the activity islands are not completely surrounded by inactives. The unbounded edges of the islands may suggest synthetic directions to take which could extend the scope of the chemistries involved. The exact nature of such direction is very context dependent, and is best identifying the structures near the unbounded edge. Finding activity for compound 26 in FIG. 8 with respect to some (hypothetical) target receptor would suggest synthesis of methoxymethyl- or hydroxyethylcyclohexyl homologs, or of hydroxymethyl-cyclopentyl or hydroxymethyltetrahydrofuranyl amine analogs, for example. Finding activity for 28, on the other hand, would suggest synthesis of pyridone or furanyl analogs. A quick similarity search carried out against known inactives would then show whether such compounds do indeed represent a real boundary in structural space.

No summary statistic which could accomplish this as effectively as direct visual inspection of FIG. 10C does is known in the prior art.

A four-point pharmacophore model for the target enzyme was formulated in connection with the kinase research project. When this pharmacophore hypothesis was employed as a query in a UNITY 3D flex search, it "hit" 67% of the actives and 26% of the inactives, but only 1% of the more generalized database of drug-like molecules represented by Chapman and Hall's Directory of Pharmacological Agents. FIG. 10D shows the plot obtained by applying the modified NLM procedure (h=0.3) of this invention to an initial PCA for all actives which matched the proposed pharmacophore together with "hits" from the same number of inactives selected at random.

The actives in FIG. 10D are distributed in a very similar pattern to those in FIG. 10C, indicating that the query captures something quite real about available binding sites on the target enzyme. The similarity between the two maps testifies to the value of using PCA to get consistent starting coordinates and to how robust the unfolding by the modified NLM is. Moreover, the general disorganization of the inactives away from the islands of activity indicate that such "hits" are probably non-specific, in that the structural classes to which they belong to characteristically present the pharmacophore of interest.

Two compounds (61 and 71) which are outliers in FIG. 10C show up in doubleton "islands" in FIG. 10D. This is because all compounds "hit" by the query were used to generate the latter map, whereas only one of each pair happened to get selected for the random sample used to generate the former. The two pairs fall well off to the right in FIG. 10D, reflecting their isolation from other "hits" in structural (fingerprint) space.

The roots of the inadequacy of both PCA and standard NLM for projecting combinatorial libraries from fingerprint space down into two dimensions become clearer when one considers some details of how compounds in such libraries are typically distributed in structural space and illuminates the reason that introducing an horizon is so effective.

To begin with, the useful dynamic range of the Soergel distances within a combinatorial library is limited if there is any scaffold to speak of. The smallest distance between any two of the 300 compounds shown in FIGS. 5–8, for example, is 0.163, whereas the largest distance is only 0.714. This is less than a four-fold range, yet it spans the spectrum from near redundancy in an HTS context to essentially no expected relationship in biochemical activity.

In addition, the high dimensionality of fingerprints makes it easy to generate nearly symmetrical relationships which cannot be displayed accurately in two dimensions. All 21 pairwise Soergel distances between compounds 1, 2, 3, 5, 6, 9 and 11 (FIG. 6), for example, fall between 0.424 and 0.527. In other words, they form a slightly irregular six dimensional simplex. Even a tetrahedron, which is only a three dimensional simplex, cannot be projected into two dimensions without severe distortion. Absent interactions with other points, a perfectly regular six dimensional simplex will be projected as a regular heptagon—hence the tendency towards round, isotropic maps when "ordinary" NLM is applied in this situation.

That long-range, high-dimensional relationships do exist within these data sets is clear from the principal component analyses used to derive starting points for the NLM. The first and second principal components obtained for the sulfonylpiperidine library (FIG. 5A) capture only 5.8 and 4.9%, respectively, of the total variance in the corresponding fingerprints, for example; extending the projection up to ten components (dimensions) only captures 28.7% more, for a total of 43.6%. Indeed, it would take a reduced descriptor space of 62 dimensions to capture 85% of the variance for this data set. PCA statistics from the more diverse kinase data set (FIG. 10A) are even more daunting: the first two components capture 14.5% of the total variance, the first ten components capture 34%, and 108 components are required to account for 85% of the original fingerprint variance.

The modified NLM procedure could, of course, be initiated using random starting coordinates, which would in many cases produce projections with comparably low stress. The key reason to use principal components is not their explanatory power but the continuity they bring to projections obtained from overlapping subsets: random initialization would obliterate the commonalities of pattern between FIGS. 10C and 10D, for example.

Cutting off long range effects in these projections by introducing an horizon allows the maps to relax, essentially by letting them unfold. For the modified NLM maps for the 300 compound subset, for example, the total stress S falls sharply as the horizon shrinks—from 5151 for h=1.0 to 4747, 2403, 1151 and 253 for h=0.65, 0.50, 0.40 and 0.30, respectively. This reduction comes in part from defining away long-range stress, but it can also be interpreted as eliminating distracting sources of long-range noise which are irreconcilable anyway. Less information is actually discarded than one might expect: the 9292 pairwise distances which fall within the horizon of 0.4 used to create FIG. 5C imply that, on average, each compound "sees" about 136 neighbors; 233 neighbors, on average, fall within 0.5 of each compound, and 57 fall within an horizon of 0.3.

Fifty seven compounds can still support some relatively high dimensional relationships, however. It is evident from the data presented here that fingerprint spaces defined by chemical libraries in general, and by combinatorial libraries in particular, are locally "flat" networks embedded at all angles in a mostly empty space, somewhat like the snowflakes making up a snowdrift. That they can be unfolded while preserving local detail and connectivity seems reasonable, given the constraints that chemical connectivity and feasibility of synthesis put on incremental structural changes and the vast diversity which is synthetically accessible. The result is that the local dimensionality around any single compound is usually much lower than is that of the library as a whole.

Setting an NLM horizon at or near a Soergel distance of 0.3 defines neighborhoods within which the effective dimensionality is low enough that meaningful projection into two dimensions is possible. It is fortunate that this natural scale of unfolding conserves relationships between individual structures and between structural classes, while also making possible informative projections of biological activity into the unfolded structural space which results. This will certainly not be the case for all high-dimensional descriptor spaces; where it does hold true, however, the method described in this patent document may prove more generally useful.

General Considerations of Visualization Methodology

The description of the invention thus far has utilized fingerprints as an example of a high-dimensional molecular descriptor which can be visualized in two dimensions. Other descriptors are, of course, well known and can be employed with the method of this invention. Four additional high dimensional descriptors can also be used to illustrate the method of adding new descriptors in a general way. Molecular holograms are simply fingerprints extended to track the number of occurrences of each fragment to replace the binary presence/absence bit. Holograms have proven to be valuable in predicting activity (Tripos, 1997). Atom pairs (Sheridan et al, 1994) are vectors which describe the number of bonds between all important molecular features. Pharmacophoric triplets (Pickett et al, 1996) intuitively relate to the medicinal chemist's view of how a compound docks at a receptor site, and at least for exploring within chemical series it appears to be useful for optimizing compound affinity. The MolConn molecular connectivity descriptors (Kier and Hall) have a long history of use in small series and can now be tested on larger ones.

However, at the present time not all high-dimensional descriptors may be utilized with the combination of PCA and modified NLM. Shape descriptors are particularly difficult, because the alignment and conformational adjustments involved in finding the best match between two molecules means that a molecule does not have a single shape. The distances among three molecules need not obey the triangle inequality (distance from A to B can be larger than the sum of distance A to C plus distance C to B). Similar behavior occurs in protein homology scoring—the best sequence alignment for any one protein depends on the other protein. In effect, these unusual descriptors call for each new molecule to appear at more than one place in the visualization map, since it is seen differently by each molecule to which it is compared. Clearly, however, the method of this invention works well with molecular descriptors which associate with each molecule a fixed vector of numbers.

The software code to perform the visualization of this invention is contained in the Code Appendix. The points which form the projected map determined by the program may be displayed in Excel or any other program, custom or commercially sold, which can display scatter plots. As noted earlier, additional display code, which does not form a part of the present invention, can be implemented in JAVA or some other language by those skilled in the art to aid in exploring the two dimensional plots and to provide access to the molecular structure which corresponds to each point in the display. Such code was used to provide FIGS. 2, 8, and 9.

REFERENCES

[1] MDL Information Systems, Inc., 146000 Catalina Street, San Leandro Calif. 94577
[2] Daylight Chemical Information Systems, Inc., 27401 Los Altos, Mission Viejo Calif. 92691
[3] UNITY is distributed by Tripos, Inc., 1699 S. Hanley Rd., St. Louis Mo. 63144
[4] Willett, P. Chemical similarity searching. *J. Chem. Inf. Comput. Sci.* 1998, 38, 983–996.
[5] Brown, R. D., and Martin, Y. C. Use of structure-activity data to compare structure-based clustering methods and descriptors for use in compound selection. *J. Chem. Inf. Comput. Sci.* 1996, 36, 572–584.
[6] Matter, H., and Lassen, D. Compound libraries for lead discovery. *Chemica Oggi* 1996, 6, 9–15.
[7] Patterson, D. E., Cramer, R. D., Ferguson, A. M., Clark, R. D. and Weinberger, L. E. Neighborhood behavior: a useful concept for validation of molecular diversity descriptors, *J. Med. Chern.* 1996, 39, 3049–3059.
[8] Matter, H. Selecting optimally diverse compounds from structure databases: a validation study of two-dimensional and three-dimensional molecular descriptors. *J. Med. Chem.* 1997, 40, 1219–1229.
[9] Wild, D. J., and Blankley, C. J. Comparison of 2D fingerprint types and hierarchy level selecection metrhods for structural grouping using Ward's clustering. *J.Chem. Inf. Comput. Sci.*, in press.
[10] Willett, P., and Winterman, V. A comparison of some measures for the determination of inter-molecular structural similarity. *Quant. Struct.-Act. Relat.* 1986, 5, 18–25.
[11] Barnard, J. M., and Downs, G. M. Clustering of chemical structures on the basis of two-dimensional similarity measures. *J. Chem. Inf. Comput. Sci.* 1992, 32, 644–649.
[12] Gower, J. C. Measures of similarity, dissimilarity and distance. In: *Encyclopedia of Statistical Sciences, Vol 5*; Kotz, S., and Johnson, N. L., Eds., John Wiley & Sons, New York, 1985, Vol. 5, pp. 397–405.
[13] Available Chemicals Directory is distributed by MDL Information Systems, Inc., 146000 Catalina Street, San Leandro Calif. 94577.
[14] ChemEnlighten is a registered trademark of Tripos, Inc., St, Louis Mo. 63144
[15] Lipinski, Calif., Lombardo, F., Dominy, B. W., and Feeney, P. J. Experimental and computational approaches to estimate solubility and permeability in drug discovery and development settings. *Adv. Drug Delivery Rev.*, 1997, 23, 3–25.
[16] CLogP is a product of BioByte, Inc., Pomona Corporation
[17] Patent pending. OptiSim is a registered trademark of Tripos, Inc., 1699 S. Hanley Rd., St. Louis Mo. 63144.
[18] Clark, R. D. OptiSim: An extended dissimilarity selection method for finding diverse representative subsets. *J. Chem. Inf Comput. Sci.* 1997, 37, 1181–1188.
[19] Clark, R. D. and Langton, W. J. Balancing representativeness against diversity using optimizable K-dissimilarity and hierarchical clustering. *J. Chem. Inf. Comput. Sci.* 1998, 38, 1079–1086. [20] Ash, S., Cline, M. A., Homer, R. W., Hurst, T., and Smith, G. B. SYBYL line notation (SLN): a versatile language for chemivcal structure representation. *J. Chem. Inf. Comput. Sci.* 1997, 37, 71–79.
[21] SYBYL is distributed by Tripos, Inc., St, Louis Mo. 63144
[22] Judson, R. Genetic algorithms and their use in chemistry. In: *Reviews in computational chemistry*, Lipkowitz, K. B., and Boyd, D. B., Eds., VCH Publishers, New York, 1997, Vol. 10, pp. 1–73.
[23] Martin, E. J., Blaney, J. M., Siani, M. A., Spellmeyer, D. C., Wong, A. K., and Moos, W. H. Measuring diversity: experimental design of combinatorial libraries for drug discovery. *J. Med. Chem.* 1995, 38, 1431–1436.
[24] Shemetulskis, N. E., Dunbar, J. B., Jr., Dunbar, B. W., Moreland, D. W., and Humblet, C. Enhancing the diversity of a corporate database using chemical database clustering and analysis. *J. Comput. -Aided Mol. Design* 1995, 9, 407–416.
[25] Sammon, J. W. A nonlinear mapping for data structure analysis. *IEEE Trans. Comput.* 1969, C-18, 401–409.
[26] B. R. Kowalski and C. F. Bender. *J. Am. Chem. Soc.* 1973, 95, 686–692.

[27] D. Domine, J. Devillers, M. Chastrette and W. Karcher. Non-linear mapping for structure-activity and structure-property modelling. *J. Chemometrics* 1993, 7, 227–242.

[28] Hudson, B., Livingstone, D. J., and Rahr, E. Pattern recognition display methods for the analysis of computed molecular properties. *J. Comput.-Aided Mol. Design* 1989, 3, 55–65.

[29] Agrafiotis, D. K. Stochastic algorithms for maximizing molecular diversity. *J. Chem. Inf. Comput. Sci.* 1997, 37, 841–851.

[30] Flower, D. R. On the properties of bit string-based measures of chemical similarity. *J. Chem. Inf. Comput. Sci.* 1998, 38, 379–386.

[31] Patent pending.

[32] Gillet, V. J., Willett, P., and Bradshaw, J. The effectiveness of reactant pools for generating structurally-diverse combinatorial libraries. *J. Chem. Inf. Comput. Sci.* 1997, 37, 731–741.

[33] Delaney, J. S. Assessing the ability of chemical similarity measures to discriminate between active and inactive compounds. *Mol. Diversity* 1995, 1, 217–222.

TABLE 1

Substructure exclusions included in the files specified by the -notlist option in 2D UNITY searches

| UNITY Query | SLN for excluded substructures | Targets |
|---|---|---|
| CH2N[f]H2 | CHN[not = NHC(=O)].C[not = C; Any]NH | polyamines |
| CS(=O)(=O)Cl | CHN[not = NHC(=O)] | free amines |
|  | S(=O)(=O)Hal. S(=O)(=O)Hal | polysulfonyl halides |
| Both | C(=O)OH | free acids |
|  | C(=O)O[f] | carboxylate salts |
|  | C(=Het)Hal | reactive halides |
|  | OH.OH | polyols |
|  | C(=Het)NH.C(=Het)NH |  |
|  | N[not = NHC(=O)]HN[not = NHC(=O)]H | hydrazines |
|  | C(=Het)N.C(=Het)N.C(=Het)N | peptides |
|  | C[is = C – Any =: Any]HZ{Z:Cl, Br, I} | activated halides |
|  | N(~O[f]) ~ O[f] | nitro compounds |
|  | F.F.F.F.F.F | perfluoroalkyls > C2 |
|  | CCCCCCCCH3 | long alkyls |
|  | H[I = 2] | heavy isotopes |
|  | H[I = 3] | " |
|  | C[I = 13] | " |
|  | C[I = 14] | " |
|  | N[I = 15] | " |
|  | S[I = 35] | " |
|  | P[I = 32] | " |

TABLE 2

Statistics and secondary filters applied to primary reagent lists.

| | Primary Amines | | Sulfonyl Chlorides | |
|---|---|---|---|---|
| Property | Cutoff | Passed | Cutoff | Passed |
| Single structure | — | 436 | — | 178 |
| Molecular weight | 200 | 361 | 350 | 163 |
| Molecular volume ($Å^3$) | 190 | 363 | 255 | 165 |
| ClogP | 2.6 | 370 | 5.0 | 168 |
| Aromatic ring count | 1 | 394 | 2 | 171 |
| Combined filters | — | 308 | — | 154 |

What is claimed is:

1. A method of visualizing in two dimensions the distance relationships in high-dimensional diversity space of compounds which are characterized by high-dimensional molecular structural descriptors comprising the steps of:

a) selecting a representative subset of the compounds;

b) evaluating the molecular structural descriptor characteristic of each compound of the subset selected;

c) based upon the molecular structural descriptors, generating a distance matrix between every pair of compounds or utilizing a function to generate the distance matrix elements between every pair of compounds as needed;

d) based upon the compound distance matrix, computing a hierarchy of clusters by defining cluster centers and partitioning the compounds at each level of clustering;

e) performing a principal component analysis (PCA) on the molecular structural descriptors characteristic of each compound utilizing the first two PCA components;

f) using a modified stress function which reflects a horizon, running a non-linear mapping (NLM) refinement from the initial PCA coordinates resulting from utilizing the first two PCA components; and g) graphically displaying the NLM generated coordinates of each compound as determined by the NLM refinement.

* * * * *